(12) United States Patent
Ackerman et al.

(10) Patent No.: US 7,574,248 B2
(45) Date of Patent: Aug. 11, 2009

(54) METHOD AND APPARATUS FOR QUANTITATIVE BONE MATRIX IMAGING BY MAGNETIC RESONANCE IMAGING

(75) Inventors: Jerome L. Ackerman, Newton, MA (US); Melvin J. Glimcher, Boston, MA (US); Yaotang Wu, Watertown, MA (US)

(73) Assignee: General Hospital Corporation, Boston, MA (US)

( * ) Notice: Subject to any disclaimer, the term of this patent is extended or adjusted under 35 U.S.C. 154(b) by 900 days.

(21) Appl. No.: 10/514,616

(22) PCT Filed: May 19, 2003

(86) PCT No.: PCT/US03/15801

§ 371 (c)(1),
(2), (4) Date: Nov. 16, 2004

(87) PCT Pub. No.: WO03/096899

PCT Pub. Date: Nov. 27, 2003

(65) Prior Publication Data

US 2005/0240096 A1    Oct. 27, 2005

Related U.S. Application Data

(60) Provisional application No. 60/381,161, filed on May 17, 2002.

(51) Int. Cl.
*A61B 5/05* (2006.01)
*G01V 3/00* (2006.01)
(52) U.S. Cl. ...................... 600/410; 324/309
(58) Field of Classification Search ......... 600/410–435; 324/300–322
See application file for complete search history.

(56) References Cited

U.S. PATENT DOCUMENTS

| | | | |
|---|---|---|---|
| 4,431,968 A | 2/1984 | Edelstein et al. |
| 4,510,450 A | 4/1985 | Brown |
| 4,635,643 A | 1/1987 | Brown |
| 4,775,522 A | 10/1988 | Clark, Jr. |
| 4,871,967 A | 10/1989 | Rotem et al. |
| 4,902,973 A | 2/1990 | Keren |
| 4,922,915 A | 5/1990 | Arnold et al. |
| 4,939,464 A | 7/1990 | Hammer |

(Continued)

OTHER PUBLICATIONS

Wu et al.; "Evaluation of Bone Mineral Density Using Three-Dimensional Solid State Phosphorus-31 NMR Projection Imaging;" Calcified Tissue International (1998) Springer-Verlag New York Inc.; 62:512-518.

(Continued)

*Primary Examiner*—Eric F Winakur
*Assistant Examiner*—Michael T Rozanski
(74) *Attorney, Agent, or Firm*—Quarles & Brady LLP

(57) ABSTRACT

An apparatus and technique for measuring volumetric, 3-D bone organic matrix density is described. The techniques includes providing a first pulse sequence fragment selected to suppress at least two fluid resonance signals and providing a second pulse sequence fragment which images at least solid signals. In one embodiment, a series of RF pulses used to suppress fluid in the bone marrow spaces, particularly in cancellous bone tissue, is combined with solid state projection reconstruction magnetic resonance imaging (MRI) to provide a three-dimensional image of a bone in which the dominant signal arises substantially from solid organic bone matrix.

17 Claims, 10 Drawing Sheets

U.S. PATENT DOCUMENTS

| | | | |
|---|---|---|---|
| 5,247,934 A | 9/1993 | Wehrli et al. |
| 5,250,899 A | 10/1993 | Listerud et al. |
| 5,270,651 A | 12/1993 | Wehrli |
| 5,281,917 A | 1/1994 | Santyr |
| 5,322,065 A | 6/1994 | Leunbach |
| 5,539,309 A | 7/1996 | Van Wyk et al. |
| 5,772,592 A | 6/1998 | Cheng et al. |
| 5,789,021 A | 8/1998 | Dooms et al. |
| 5,910,972 A | 6/1999 | Ohkubo et al. |
| 5,931,795 A | 8/1999 | Manly et al. |
| 6,010,681 A | 1/2000 | Margerum et al. |
| 6,185,444 B1 | 2/2001 | Ackerman et al. |
| 6,249,692 B1 | 6/2001 | Cowin |
| 6,285,901 B1 | 9/2001 | Taicher et al. |
| 6,320,931 B1 | 11/2001 | Arnold |
| 6,430,427 B1 | 8/2002 | Lee et al. |
| 6,442,287 B1 | 8/2002 | Jiang et al. |
| 6,449,502 B1 | 9/2002 | Ohkubo |
| 6,490,339 B2 | 12/2002 | Mitchell et al. |
| 6,510,197 B1 | 1/2003 | Mitchell et al. |
| 6,516,045 B2 | 2/2003 | Shepherd et al. |
| 6,560,477 B1 * | 5/2003 | Filler | 600/410 |
| 6,653,832 B2 * | 11/2003 | Wind et al. | 324/307 |
| 7,288,936 B2 * | 10/2007 | Larson et al. | 324/307 |

OTHER PUBLICATIONS

PCT Search Report; PCT/US03/15801; dated Sep. 17, 2003.
Wu; "Density of Organic Matrix of Native Mineralized Bone Measured by Water and Fat Suppressed;" Magnetic Resonance In Medicine Manuscript MRM-102-6049; Feb. 19, 2003; pp. 1-38.

* cited by examiner

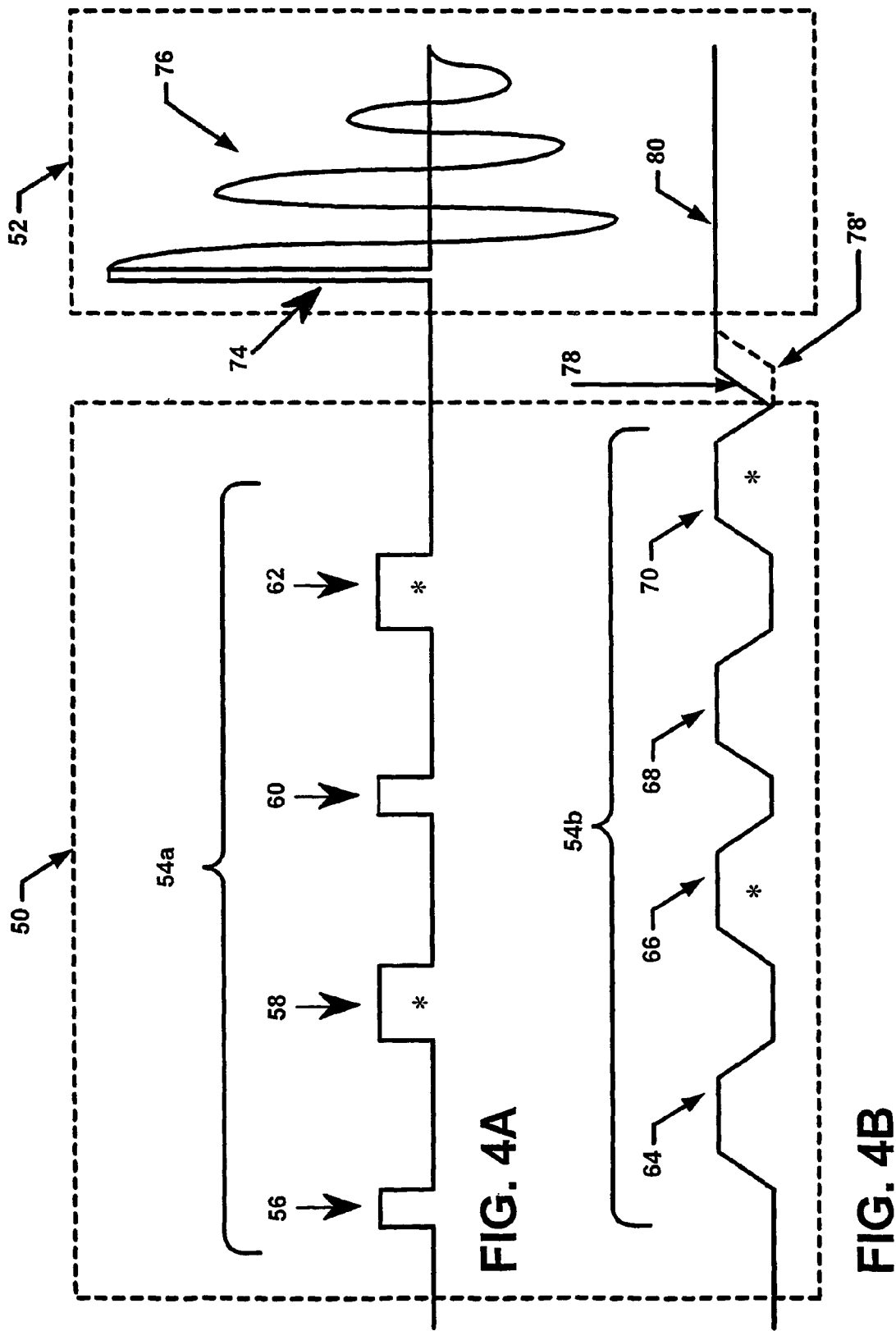

METHOD AND APPARATUS FOR QUANTITATIVE BONE MATRIX IMAGING BY MAGNETIC RESONANCE IMAGING

CROSS-REFERENCE TO RELATED APPLICATIONS

This application is a National Stage application, of and claims the benefit of PCT Application No. PCT/US03/15801, filed on May 19, 2003, which claims the benefit of U.S. Provisional Application No. 60/381,161, filed on May 17, 2002, which are incorporated herein by reference.

FIELD AND BACKGROUND OF THE INVENTION

This invention relates generally to magnetic resonance imaging (MRI) and more particularly to a method and apparatus for measuring the degree of volumetric (3-D) bone organic matrix density.

Glossary of Currently Used Terms to Describe the Structure, Composition and Organization of "Bone"

The term "bone" may be used to refer to various levels of bone structure, composition and organization, from the gross visual, naked eye identification of a specific whole bone or a part of a whole bone such as the femur (the upper bone of the thigh), viz., "bone" as an organ or a part of an organ, to the specific structural organization of portions of a bone by light microscopy, that is, of "bone" as a tissue, e.g., compact bone or cancellous (spongy or trabecular) bone, or even to the organization of the individual components of bone tissue, that is, "bone" as a substance or material (bone substance) whose individual components can be visualized, for example, by electron microscopy and other techniques.

FIGS. 1A, 1B and 1C show the cylindrical portion of the diaphysis (shaft) of an animal's tibial bone (portion of a whole gross bone). The bone material or substance is densely packed—thus the cylindrical wall of the bony shaft, the bone tissue, is described as compact bone. At the ends of a long bone, the bone as an organ, for example, the head and neck regions of the femur, the bone substance is not densely packed. Indeed, the bone tissue is clearly organized in a specific three-dimensional, loosely packed interconnected open network consisting of small segments of bone substance referred to as trabeculae, and the bone tissue referred to as cancellous or spongy or trabecular bone tissue.

The basic bone substance or material is composed principally of a soft matrix consisting primarily of the (fibrous) protein collagen and small amounts of other organic constituents and other extracellular, extravascular organic constituents and is referred to as the organic matrix of bone substance. It is into this matrix that the other major component of bone substance, the hard crystals of calcium-phosphate ("apatite") (solid mineral phase), is deposited. Therefore, the two major components of bone substance are: (1) a soft organic matrix and (2) the hard solid phase of the calcium-phosphate crystals, the solid mineral phase. These two components provide a good portion of the mechanical properties of bone as an organ, a tissue and a material substance, as well as many of the physiological functions of bone substance. The organic matrix of bone substance is ordinarily considered to consist of the extracellular, extravascular organic components of the bone substance and the bone tissue, and is chemically analyzed by measuring the collagen or collagen and other known proteins and organic constituents of the extracellular, extravascular matrix.

The composition of the bone substance can therefore be expressed in terms of the relative proportions of the two major constituents of bone substance, either by the weight percentages of the two major components, viz., the weight percentage of the organic matrix compared with the weight percentage of the solid mineral phase, or better still, by consideration of the volumetric density of the solid mineral phase and, independently, of the volumetric organic matrix density: it is much more important and informative to be able to express the composition of bone substance and of bone tissue in terms of volume, e.g., the mass or weight of the solid mineral phase in a unit volume of bone substance ($gm/cm^3$), and the volumetric density of the mass or weight of the organic matrix in a unit volume of bone substance in $gm/cm^3$. From these data, viz., the volumetric density of the solid calcium-phosphate mineral phase and the volumetric density of the soft organic matrix, it is possible to calculate the extent or degree of mineralization, that is, the extent to which a unit volume of bone substance in compact or cancellous bone tissue is mineralized. This has not been accomplished previously by any noninvasive technique but has been accomplished as described in this patent application. Because this invention accomplishes the measurement of bone organic matrix density by MRI, no ionizing radiation is used, and therefore patients may be examined repeatedly without the risk associated with ionizing radiation.

We therefore use the following terms and definitions: (1) bone mineral density; (2) bone organic matrix density (organic matrix density of bone); (3) extent (or degree) of bone mineralization. It is important to distinguish, however, whether these data have been calculated from 2-D (areal) measurements and not measured as 3-D volumetric data, or have been directly measured as volumetric 3-D data, as accomplished by the techniques described in this patent application. It is from these directly measured volumetric data that it is possible to calculate the volumetric extent or degree of mineralization of bone substance non-invasively. The ratio of volumetric, 3-D bone mineral density to volumetric bone organic matrix density is referred to as the extent or degree of bone mineralization.

Currently, the 3-D volumetric extent or degree of mineralization cannot be measured noninvasively. It can be determined by chemical and gravimetric analyses of a piece of bone tissue removed from a patient or an animal surgically by biopsy. Clearly, such a surgical procedure cannot be carried out each time a measurement is needed to follow the course of any particular disease or to assess the efficacy of a particular drug or treatment over a long, extended period of time.

Techniques for measuring bone mineral density non-invasively have been developed. Two such techniques are by X-ray and magnetic resonance imaging (MRI). Prior to this invention, no noninvasive methods for measuring volumetric bone matrix density had been described.

Currently, two of the most commonly used techniques to measure bone mineral density are: (1) dual energy x-ray absorptiometry (DXA) and (2) computed tomography (CT). DXA utilizes x-rays of two energies. The mineral and soft tissue each exhibit different x-ray scattering cross sections at each energy level, enabling a map of mineral density to be computed from the scan data. However, because of the variable composition of the soft tissue and its variable depth along the view direction, overlapping bone structure and the inhomogeneity of the 3-D spatial distribution of the trabeculae in cancellous bone, for example, the most commonly analyzed bone tissue using this technique, the 2-D (areal) measurement of bone mineral density may not reflect the true volumetric 3-D bone mineral density. Indeed, serious questions have been raised in the literature about the validity and usefulness of the data obtained by DXA.

Computed tomography (CT) produces an accurate measurement of volumetric, 3-D bone mineral density (grams per cubic centimeter). However, when the x-ray intensity is sufficient to make the CT scan quantitatively accurate (quantitative CT or QCT), the radiation dose to the patient is high, limiting the number of scans permissible for a single patient, thus preventing the use of QCT on women of child bearing age, growing children and patients who may require repeated measurements in order to follow and assess the course of a disease or injury or to assess the efficacy of treatment. Like any x-ray based measurement, CT does not distinguish bone matrix from soft tissue, and is susceptible to errors because of the variability of soft tissue composition and depth.

Measurement of the Volumetric (3-D) Density of the Organic Matrix of Bone by Proton Nuclear Magnetic Resonance Imaging Magnetic resonance imaging (MRI) is a widely used and highly effective means of producing two and three dimensional images of the body. With suitable settings of the parameters of the pulse sequence (e.g. the definition of the timing, amplitude, frequency, phase and other details of the radio frequency and magnetic field gradient pulses and various control functions produced by the scanner) MRI can yield quantitative data on certain properties of tissues.

Conventional proton MRI detects the fluid proton (hydrogen) content of soft tissues, which is mainly liquid water, and to a lesser extent, fat. However, most solid substances, including bone substance, do not yield signals in conventional MRI, and thus are not detected and therefore not very visible in conventional MRI. Conventional MRI therefore yields no information on the composition of the bone substance To obtain MR images of solid materials, it is necessary to utilize specialized pulse sequences and scanner hardware.

The Larmor (resonance) frequency of a nuclear spin is proportional to a constant (the magnetogyric ratio) specific to each nuclear species, as well as proportional to the total magnetic field in which it is immersed. During MR scanning nuclear spins in a material or body experience both the strong magnetic field of the scanner as well as the smaller local magnetic fields of neighboring nuclear spins. The instantaneous sum of all these fields at the site of a particular spin determines its Larmor frequency. In the most general case of a solid, a particular spin will experience a local field dependent on the number, spatial location and quantum state of all the other spins in its vicinity, in addition to the much stronger field of the scanner. This effect is called dipole-dipole, or spin-spin, coupling. Different spins will experience somewhat different local fields, but all spins will experience the same scanner field. Therefore the Larmor frequencies will be distributed about a central value (determined by the scanner field), yielding a frequency spectrum having a finite line width.

If the spins are widely separated from each other in the material, the spectral line width will be relatively small. If the spins are in fast random relative motion with respect to each other (as in the case of a fluid such as liquid water), such that the local field is rapidly time dependent with a short autocorrelation time, the effective local field is averaged to zero, and the line width will be very small. For the case of typical organic solids, the proton line width may be on the order of several thousand Hertz (Hz) to several tens of kilohertz (kHz). For fluid systems the proton frequency spectrum line width may be on the order of less than 1 Hz to a few hundred Hz.

The line width strongly affects the performance of MR imaging. The inverse of the spectral line width is generally known as $T_2$ if the spectral broadening is due to spin-spin coupling among like (homogeneous, e.g., all proton) spins, and $T_2^*$ if the spectral broadening is due to a static (not time dependent) distribution of the intrinsic Larmor frequency unrelated to homogeneous spin-spin coupling. Both types of broadening mechanisms are often present, and $T_2^*$ is usually used to denote the total broadening of the spectral line. Therefore, in the remainder of the invention description $T_2^*$ will be used in the conventional manner to encompass all the spectral line broadening effects intrinsic to the subject or specimen as well as due to scanner main magnet inhomogeneity. $T_2^*$ represents the characteristic time for the MR signal to dephase following an RF pulse, and imposes a limit on both the spatial resolution and the signal-to-noise ratio obtainable in an image. Because the spectral line widths of solid materials, such as bone matrix, are usually far larger than those of fluid materials, such as tissue water or fat, it is expected that images of solid materials are of much lower spatial resolution and signal-to-noise ratio.

Following the initial RF pulse which elicits a transverse magnetization (the detection and recording of which constitutes the MR signal), the magnetization begins to dephase under the dipole-dipole coupling and other mechanisms. Essentially all conventional MR pulse sequences require the generation and recording of a spin echo, which is the forced rephasing of the dephased signal by the application of a magnetic field gradient pulse reversal or a 180 degree (180°) RF pulse. The $T_2^*$ type of broadening may be overcome with the 180° pulse, but the $T_2$ type of broadening cannot be overcome by any simple sequence of RF pulses. Because of certain scanner engineering constraints, the minimum time between the initial RF pulse and the spin echo (the echo time, or TE) can usually be no shorter than a few milliseconds, which limits the line widths to be no greater than a few hundred Hz if the signals are to be detected. Therefore, a solid material (operationally defined here as any substance with $T_2$ less than about 1 ms), including but not limited to bone matrix, cannot be imaged with conventional MR pulse sequences.

One MRI technique which can be used to image solids is referred to as solid state MRI or projection reconstruction MR imaging or projection MRI or even more simply projection imaging. Projection imaging employs only an initial RF pulse and does not elicit spin echoes. The RF pulse elicits a magnetization response referred to as a free induction decay (FID). The FID begins to de-phase immediately following the end of the RF pulse. The FID is ignored in conventional pulse sequences, but may in fact be recorded to create a data set that can be reconstructed into an image. In simple projection imaging (without slice selection), the FID is recorded in the presence of a constant amplitude magnetic field gradient. The magnetic field gradient direction is advanced to a new direction, and the FID is elicited with an RF pulse, and recorded again. The process is repeated to cover all directions in three dimensional space, and the image is reconstructed from the recorded data using one of several possible algorithms to yield a three dimensional image. Because no spin echo is required, short $T_2$ or $T_2^*$ does not prevent the projection method from imaging solid materials. However, short $T_2$ or $T_2^*$ will still reduce the spatial resolution and signal-to-noise ratio in projection imaging just as they do in conventional MRI.

Although simple projection imaging can be used to make images of bone matrix, it has a limitation in that all proton containing substances, including bone marrow, will be imaged. Because the marrow proton signals largely arise from fluid substances (e.g. water and fat), their signals will be imaged at relatively high signal-to-noise ratio, and will dominate the signals from the matrix. Thus, since solid state MRI measures both fluid and solid constituents, it cannot be used to effectively measure the volumetric, 3-D density of the organic matrix of bone.

In summary, conventional proton MRI detects only the fluid constituents of bone and thus cannot be used to measure the volumetric, 3-D density of the organic matrix of bone. Solid state MRI, on the other hand, detects both the solid and fluid constituents of a bone and since the fluid constituents obscure the solid constituents, solid state MRI cannot be used to measure the volumetric, 3-D density of the organic matrix of bone. Thus, neither conventional proton MRI nor unmodified solid state MRI can be used to measure the volumetric density of the organic matrix of bone.

SUMMARY OF THE INVENTION

It has, in accordance with the present invention, been recognized that it would be very advantageous to provide a method for measuring the 3-D volumetric density of the organic matrix of bone since this would make possible to combine the data so obtained with the 3-D volumetric density of the bone mineral to measure the volumetric 3-D extent or degree of mineralization in bone substance.

In the present invention, projection imaging is combined with a fluid (e.g. water and fat) signal suppression technique to produce images of only the volumetric, 3-D bone organic matrix thereby enabling the measurement of the volumetric, 3-D bone organic matrix density. The water and fat signal suppression technique is selected such that water and fat signals are mostly eliminated, while the signals arising from the organic matrix are largely retained. In accordance with the present invention, the technique for measuring the volumetric, 3-D bone organic matrix density includes providing a first pulse sequence fragment selected to suppress at least two fluid resonance signals and providing a second pulse sequence fragment which images at least solid signals.

With this particular arrangement, a technique which enables quantitative three-dimensional (3D) imaging of bone organic matrix density is provided. By using a first pulse sequence fragment which suppress at least two fluid resonance signals and then using a second pulse sequence fragment which images at least solid signals, the technique of the present invention can be used to non-invasively measure the volumetric density of the bone organic matrix (in grams per cubic centimeter) over an extended volume of a particular bone. The technique of the present invention does not rely on an invasive procedure (e.g. biopsy) nor does it rely on any procedure which utilizes x-rays or other ionizing radiation. The technique of the present invention thus presents relatively little, if any, risk to the subject.

By combining a specific series of narrowband radio frequency (RF) pulses to suppress fluid (e.g. water and fat) in bone marrow with proton solid state projection reconstruction MRI, a three dimensional image of the bone in which the dominant signal arises only from the solid bone organic matrix is provided. The narrowband RF pulses substantially suppress the signals from the water, fat and other relatively mobile constituents within the marrow spaces and in the bone substance, especially in cancellous bone, while retaining a significant portion of the signals from the solid immobile organic matrix constituents of the bone substance. The present invention thus enables the quantitative three-dimensional imaging of bone organic matrix density noninvasively with solid state MRI.

Water and fat suppressed projection MR imaging thus utilizes the large difference between the proton $T_2^*$s of the solid organic matrix and the fluid constituents of bone to suppress the fluid signals while preserving the solid organic matrix signals. The solid constituents include collagen and other proteins and organic constituent signals, some molecularly immobile water, and exhibit very short $T_2^*$. The fluid constituents include molecularly mobile water and fat, with long $T_2^*$. In the technique of the present invention, chemical shift selective low power 90 degree pulses excite mobile water and fat magnetization which is subsequently dephased by gradient pulses, while the magnetization of collagen and other solid immobile organic matrix constituents of bone matrix and immobile water remains mostly in the z-direction. Additional selective 180 degree pulses in alternate scans further cancel the residual water and fat magnetization. Following water and fat suppression and acquisition of a proton bone matrix density image, this technique can be used in combination with volumetric, 3-D bone mineral density measurement by solid state $^{31}P$ projection MRI to determine the volumetric, 3-D degree or extent of bone mineralization, that is, the fraction of the total volume of bone substance occupied by the bone mineral or the grams of bone mineral in a unit volume of bone substance.

Thus, by positioning a bone in a substantially static magnetic field and subjecting the bone to a first pulse sequence fragment selected to suppress at least two fluid proton MR signals and then subjecting the bone to a second pulse sequence fragment to acquire at least a solid state proton MR image it is possible to acquire proton RF signals emitted by the bone. The proton RF signals are processed to generate data representative of the volumetric, 3-D bone organic matrix density. An additional pulse sequence may be used to acquire the solid state $^{31}p$ image of the bone. The 3-D volumetric bone mineral density and the 3-D volumetric bone organic matrix density data are then used to calculate the degree or extent of volumetric bone mineralization.

In accordance with a further aspect of the present invention, a magnetic resonance imaging (MRI) system for obtaining a quantitative bone organic matrix density measure includes an MRI pulse sequence generator for providing a first pulse sequence fragment selected to suppress at least two fluid resonance signals and for providing a second pulse sequence fragment which images at least solid signals.

With this particular arrangement, a system which provides a quantitative three dimensional image of bone organic matrix density is provided. In one embodiment, the MRI pulse sequence generator combines a series of narrowband radio frequency (RF) pulses with proton solid state projection reconstruction MRI to provide a three dimensional image of the bone in which the dominant signal arises only from the solid organic bone matrix. The narrowband RF pulses substantially suppress signals generated in response to fluids (e.g. water and fat) in bone marrow, while retaining a significant portion of the matrix signal.

Normally the solid state projection reconstruction MRI, especially of cancellous bone, would image the marrow tissue and spaces (which contains a significant amount of fluid and fat). However, since the narrowband RF pulses suppress a substantial amount of the fluid signals, the proton solid state projection reconstruction MRI provides a three-dimensional image of the bone substance in which the dominant signal arises primarily, if not totally, from the solid organic bone matrix. The system can thus provide a quantitative three-dimensional image of organic bone matrix density non-invasively with proton solid-state magnetic resonance imaging. The volumetric bone organic matrix density can then be used with data from the volumetric bone mineral density to obtain a measure of the degree of bone mineralization in a selected portion of either compact or cancellous bone tissue.

BRIEF DESCRIPTION OF THE DRAWINGS

The foregoing features of the invention, as well as the invention itself may be more fully understood from the following detailed description of the drawings, in which:

FIG. 4 is comprised of FIGS. 4A and 4B which are plots of radio frequency (RF) and magnetic field gradient pulse sequences, respectively, used to measure bone organic matrix density;

DESCRIPTION OF THE PREFERRED EMBODIMENTS

Figure 1A:
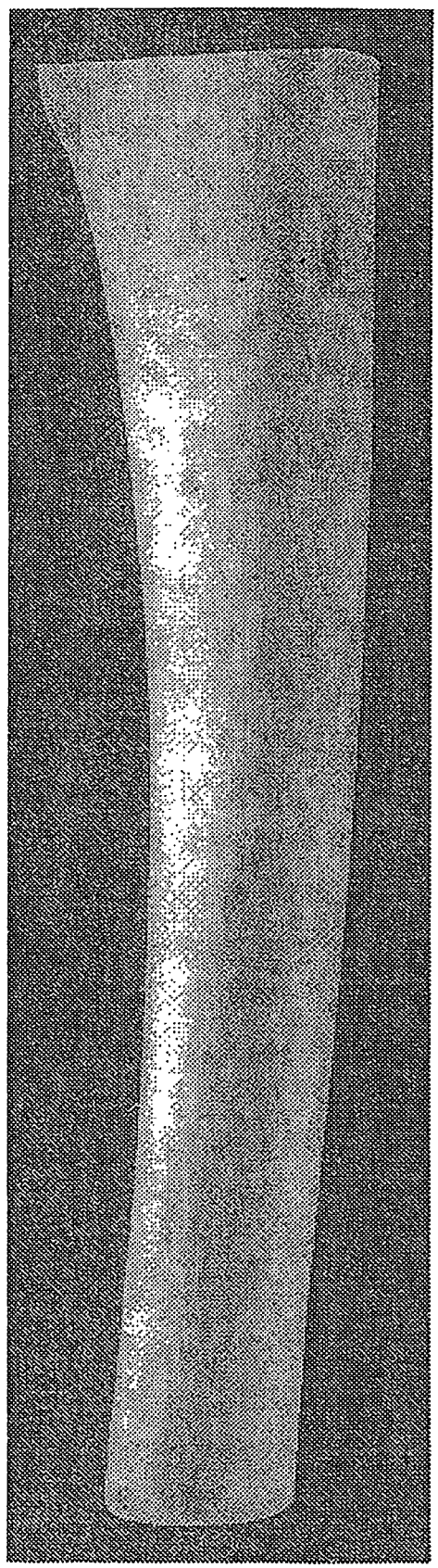
FIG. 1A, is a large portion of a tibial bone of an animal and serve as an example of bone as an organ.

Before describing a system for quantitative bone matrix imaging by solid state proton magnetic resonance imaging (MRI) system and the operations performed to produce an image which aids in the diagnosis and treatment of osteoporosis and other conditions, some introductory concepts and terminology are explained.

As mentioned above, for the case of typical organic solids, the proton line width may be on the order of several thousand Hertz (Hz) to several tens of kilohertz (kHz). For fluid systems, the proton line width may be on the order of less than 1 Hz to a few hundred Hz. Thus, the term "fluid," as used herein refers to any material yielding nuclear magnetic resonance (NMR) signals (having a spectral response) below 1 kilohertz (kHz) and the term "solid" as used herein refers to any material having a spectral response at or above 1 kHz.

Reference is sometimes made herein to providing techniques to aid in the detection of osteoporosis. It should be recognized that references made herein to any specific condition, disease, bone or bone region are made to provide clarity in the description and should not be construed as limiting. It should be appreciated that the techniques of the present invention can be equally applied to aid in the detection, diagnosis and evaluation of a variety of conditions or diseases other than osteoporosis including but not limited to osteomalacia (rickets), osteopenia, Paget's disease, osteoarthritis, osteonecrosis, cancer, fracture and any other metabolic, inflammatory, ischemic, traumatic or infectious disease or condition of bone. The present invention may also be applied in the evaluation of normal conditions of bone such as the assessment of bone growth and remodeling, or in the healing or repair of a fracture or other condition of bone, and in metabolic and endocrinological or genetic disorders or abnormalities of bone.

Reference is also made herein to measurements of bone organic matrix density for a particular bone region (e.g. the hip, the femoral neck, the wrist or a vertebral body) and that such measurements aid in the diagnosis and treatment of osteoporosis. It should also be understood that the apparatus and techniques of the present invention are not limited to computation of bone matrix density in any particular type of bone nor to diagnosis and treatment of osteoporosis. It is recognized herein that the techniques of the present invention may be applied to any type of bone including but not limited to cortical bone and trabecular (cancellous) bone and other bone regions and that examination of bone matrix density in other bone regions may be useful to aid in the diagnosis and treatment of osteoporosis and/or conditions other than osteoporosis. In addition, the techniques of the present invention may be used to detect, diagnose or evaluate conditions of other regions of the body containing bone-like tissues or materials such as implants, calcified atherosclerotic plaques, calcified heart valves, and tissues containing solid or semi-solid collagen such as cartilage, tendon, ligament, scar and other fibrotic tissues. Examination of specimens of such tissues or bone outside of the body, and of synthetic materials containing fluid and solid phases are also within the scope of the invention.

Generally, the system and techniques described herein enable measurement of bone matrix density by first suppressing fluid (e.g. water and fat signals) with a sequence of frequency selective RF pulses which precede the pulses of a solid state imaging sequence such as the field gradient pulse and RF pulse of a projection imaging pulse sequence. Because the fluid (water and fat) spectral line widths are relatively narrow compared to the line width of the bone organic matrix, and because they occur at different Larmor frequencies (separated by the chemical shift difference between water and fat), they may be excited with so-called "weak" RF pulses, which excite only a relatively narrow band of frequencies. In principle, either water or fat could be excited with a weak 90° RF pulse, which would convert all the signal of that substance, for instance water, into transverse magnetization which would then be allowed to dephase under a field gradient pulse (the dephasing gradient). In practical systems, however, it is nearly impossible to apply a perfect 90° pulse to an entire volume of a specimen or subject. Therefore, the pulse sequence may be repeated with the addition of a 180° frequency selective pulse following the first dephasing gradient. This inverts any residual water longitudinal magnetization to its inverse, which then contributes to the image, but in a negative sense. Subsequent repetitions of the pulse sequence are performed alternately with and then without the 180° pulse and its accompanying dephasing gradient, and all of the recorded signals are co-added. The residual water signals, already reduced substantially because of the 90° RF pulse and dephasing gradient pulse, are alternately positive and negative in the summation but of approximately the same magnitude, and so they largely cancel. By this method, up to about 97 percent of the water signal may be suppressed. The same process is applied to suppress the fluid fat signal. In the combined suppression, the first pulse sequence repetition contains frequency selective 90 pulses for water and fat, accompanied by their gradient dephasing pulses, while the second repetition also includes the 180° pulses for water and fat. The pairs of pulse sequences are co-added to suppress the fluid water and fat signals. By careful choice of the frequency selective pulse amplitudes (which approximately determine the frequency bandwidth over which the pulses are effective), the effect of these pulses on the signal from the solid matrix may be reduced while retaining good fluid signal suppression.

By being able to identify 3-D volumetric bone organic matrix density, the apparatus and techniques of the present invention can be used to compute a bone organic matrix density and thus aid in the diagnosis and detection of osteoporosis and a variety of different conditions in subjects. For example, by reliably measuring the bone matrix density in a particular region of interest in a subject, it may be possible to provide a non-invasive technique for assisting in the diagnoses of a variety of diseases including but not limited to osteoporosis, osteomalacia (rickets), osteopenia, Paget's disease, osteoarthritis, osteonecrosis, cancer, fracture and any other metabolic, inflammatory, ischemic, traumatic or infectious disease or condition of bone. The present invention may also be applied in the evaluation of normal conditions of bone such as the assessment of bone growth and remodeling, or in the healing or repair of a fracture or other metabolic, genetic or endocrinological disturbances of bone.

Figure 2:
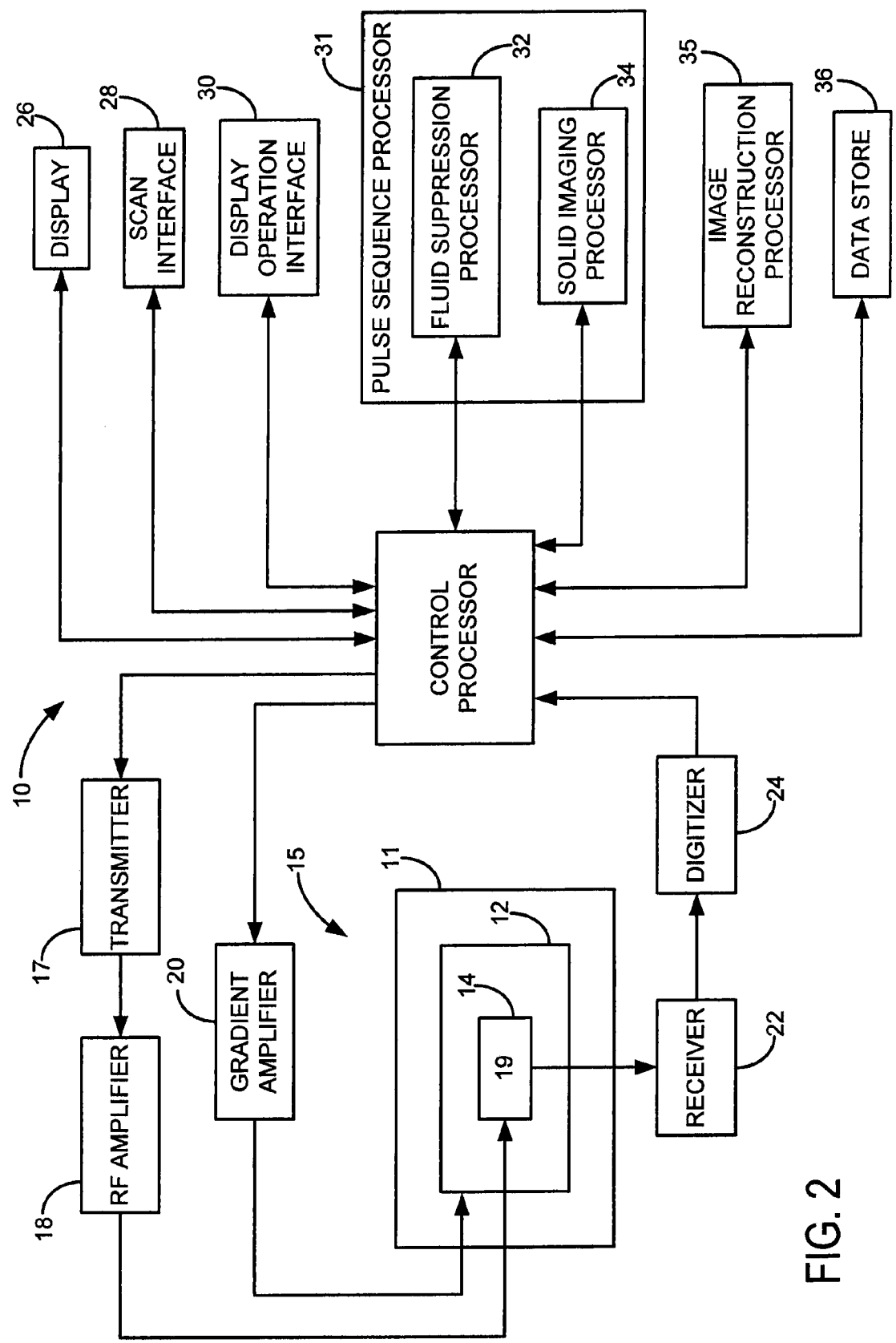
FIG. 2 is a block diagram of a system for measuring bone matrix density.

Turning now to FIG. 2, a magnetic resonance imaging (MRI) system 10 that may be programmed to non-invasively measure bone matrix density and aid in the diagnosis and detection of osteoporosis and other conditions in accordance with the present invention includes a magnet 11 having gradient coils 12 and RF coils 14 disposed thereabout in a particular manner to provide a magnet system 15. In response to control signals provided from a controller processor 16, a transmitter 17 provides a transmit signal to the RF coil 14 through an RF power amplifier 18. A gradient amplifier 20 provides a signal to the gradient coils 12 also in response to signals provided by the control processor 16.

The magnet system 15 is driven by the transmitter 17 and amplifiers 18, 20. The transmitter 17 generates a radio frequency drive signal which is amplified by the RF amplifier 18 and applied to the RF coil 14. The gradient amplifier 20 provides a magnetic field gradient drive signal which is applied to the set of gradient coils 12. The resultant magnetic field gradient may have an arbitrary direction. For generating a uniform, steady main magnetic field required for MRI, the magnet system 11 may be provided by resistive coils driven by a generator, permanent magnets, superconducting coils, or the earth's magnetic field. The magnetic fields are generated in an examination or scanning space or region 19 in which the object to be examined is disposed. For example, if the object is a person or patient to be examined, the person or portion of the person to be examined is disposed in the region 19.

The transmitter/amplifier 17,18 drive the RF coil 14. After the RF pulse is applied to the RF coil 14, spin resonance signals are generated in the object situated in the examination space 19, which signals are detected and are applied to a receiver 22. Depending upon the measuring technique to be executed, the same RF coil 14 can be used for the transmitter coil and the receiver coil or use can be made of separate coils for transmission and reception. The detected resonance signals are sampled and digitized in a digitizer 24. Digitizer 24 converts the analog signals to a stream of digital bits which represent the measured data and provides the bit stream to the control processor 16.

The control processor 16 processes the resonance signals measured so as to obtain an image of the excited part of the object. A display 26 coupled to the control processor 16 is-provided for the display of the reconstructed image. The display 26 may be provided for example as a monitor, a terminal, such as a CRT or flat panel display.

A user provides scan and display operation commands and parameters to the control processor 16 through a scan interface 28 and a display operation interface 30 each of which provide means for a user to interface with and control the operating parameters of the MRI system 10 in a manner well known to those of ordinary skill in the art.

The control processor 16 also has coupled thereto a pulse sequence processor 31 and an image reconstruction processor 35. The pulse sequence processor 31 includes a fluid suppression processor 32 and a solid imaging processor 34. Also coupled to the control processor is a data store 36. Each of the components depicted in FIG. 1, except for the pulse sequence processor 31 are standard equipment in commercially available MRI systems. It should be appreciated that the MRI system must be capable of implementing the pulse sequence provided by pulse sequence processor 31 and the MRI system must also be capable of acquiring the resultant data.

In some embodiments, the pulse sequence processor 31 may be provided as a general purpose processor or computer programmed to provide pulse sequences in accordance with the techniques described herein. In one embodiment, the pulse sequence processor 31, fluid suppression processor 32 and solid imaging processor 34 may be implemented as computer program code executed by the same physical processor or by physically separate processors. It should also be appreciated that one or more of the processors 31, 32, 34 (or all of the processors 31, 32, 34) may be implemented in hardware (e.g. as an integrated circuit such as an application specific integrated circuit (ASIC)) or a combination of hardware and software.

In some applications it may be desirable to provide a single processor or computer which is appropriately programmed to perform the functions of control processor 16, pulse sequence processor 31, fluid suppression processor 32 and solid imaging processor 34. In other embodiments, control processor 16, pulse sequence processor 31, fluid suppression processor 32 and solid imaging processor 34 may be provided as specially designed processors (e.g. digital signal processors) or other specially designed digital or analog circuits. In any event, pulse sequence processor 31 is unique in that it is programmed or otherwise designed to provide a sequence of pulses to allow measurement of the volumetric, 3-D bone organic matrix density and the detection of osteoporosis and other diseases in accordance with the present invention as described below.

The fluid suppression processor 32 and solid imaging processor 34 cooperate to provide a sequence of pulses for measuring the volumetric, 3-D bone organic matrix density. One particular pulse sequence is described below in conjunction with FIG. 3. Suffice it here to say, however, that in accordance with the present invention, fluid water and fat signals are suppressed with a sequence of frequency selective RF pulses which precede the pulses of a solid state imaging sequence such as the field gradient pulse and RF pulse of a projection imaging pulse sequence. The fluid (e.g. water and fat) chemical shift selective pulses are long duration low power rectangular RF pulses. After each selective pulse, a strong dephasing gradient destroys any transverse water or fat magnetization. Residual water or fat longitudinal magnetization is inverted on alternate scans, and is cancelled when the scans are co-added. After the train of selective RF and gradient pulses, a short duration high power nonselective RF pulse excites a portion of the remaining z-magnetization, which should consist of only short $T_2^*$ constituents (mostly solid collagen), to be read out as a free induction decay (FID) in the presence of a frequency-encoding 3D projection gradient pulse. The delay between the projection gradient ramp-up and the hard RF pulse (typically a few hundred microseconds) is chosen to permit any gradient transients to settle. By reading an FID rather than an echo, and dispensing with slice selection, the pulse sequence is designed to image materials with $T_2$ values far below the minimum echo times of most scanners.

Figure 1B:
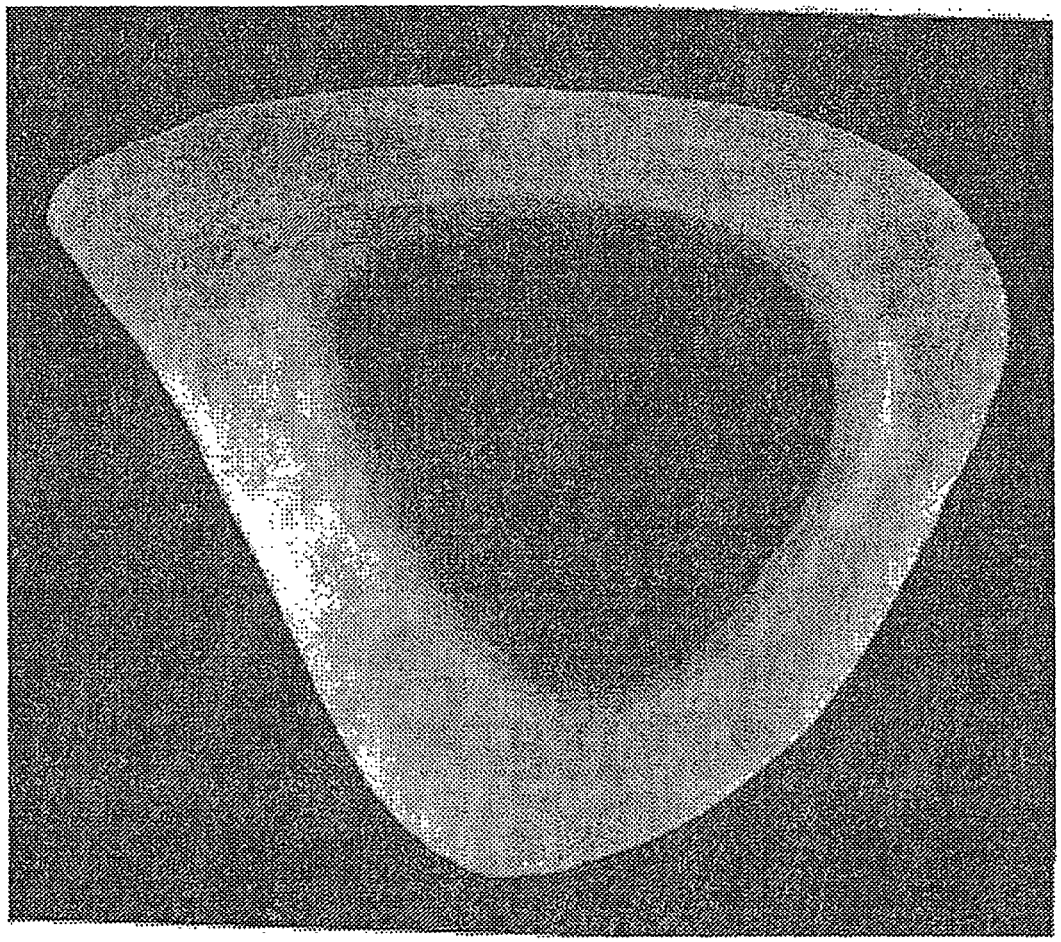
FIG. 1B is a cross sectional view of the bone shown in FIG. 1A and shows the dense compaction of the bone substance of which the organ is composed which is referred to as com-pact bone tissue.
Figure 1C:
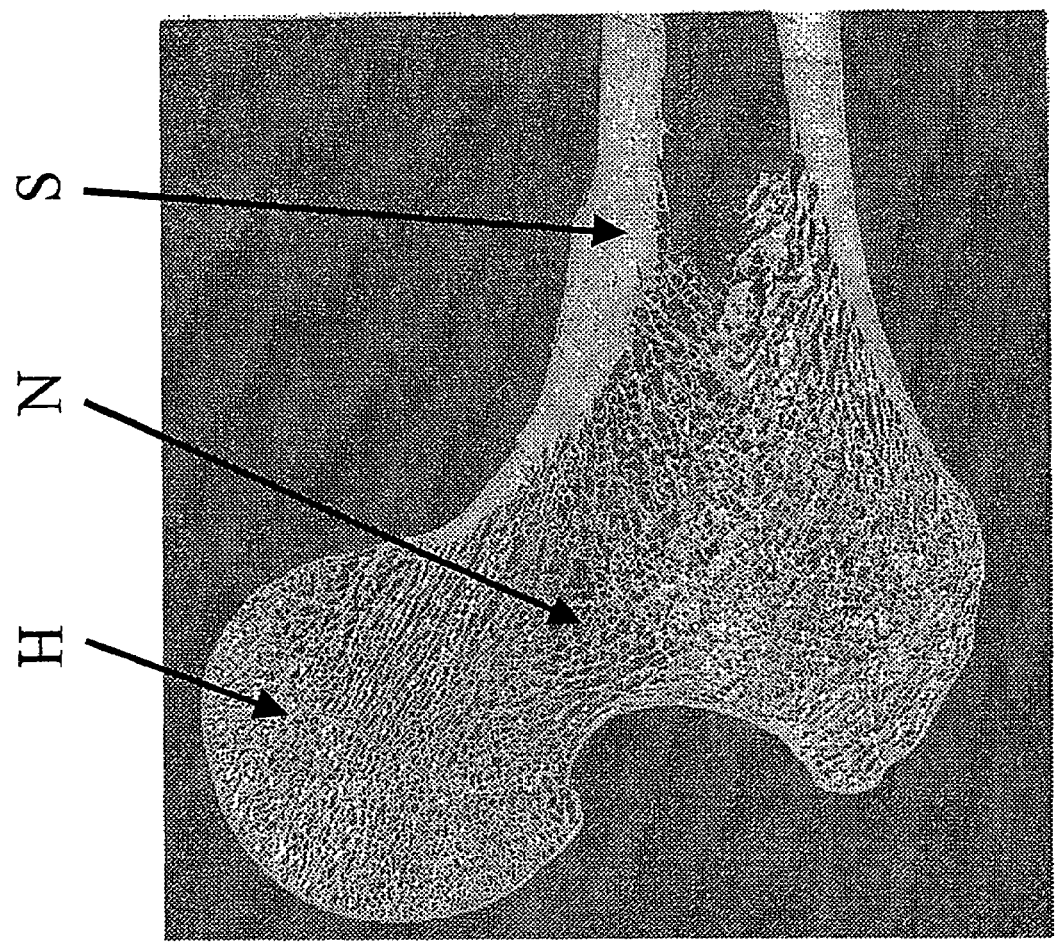
FIG. 1C is a section through a human femoral head (H), neck (N), and shaft (S); it should be noted that the femoral head, neck and portion of the trochanter consist of small pieces of bone substance (trabeculae) packed loosely in a sponge-like manner; this is referred to as cancellous bone and can be compared with the very dense compact bone in the shaft of the bone.
Figure 3:
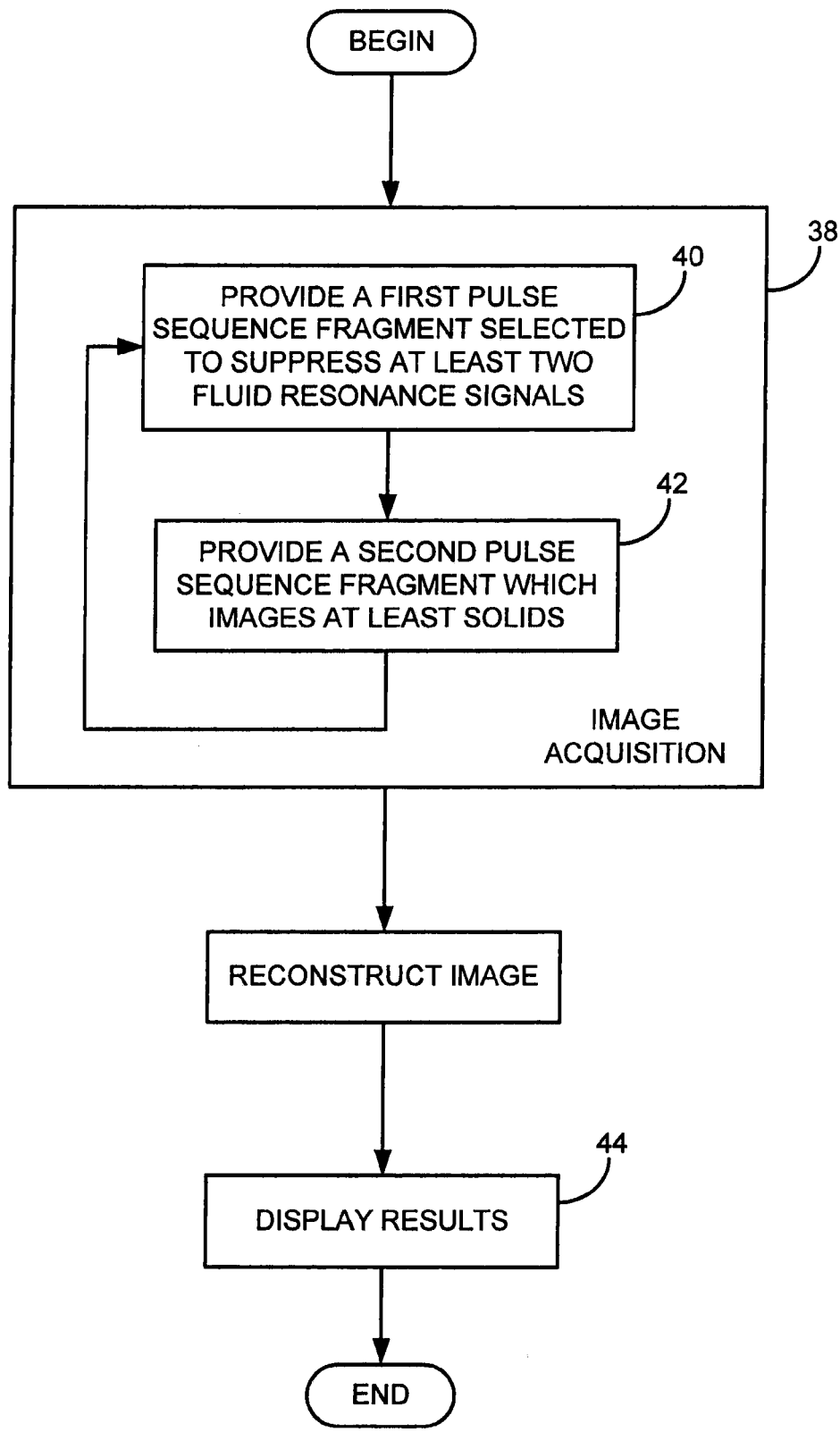
FIG. 3 is a flow diagram showing the steps in a technique for measuring bone matrix density in bone substance.

Referring now to FIG. 3, a flow diagram shows the processing performed by a processing apparatus which may, for example, be provided as part of an MRI system such as that shown in FIG. 1 to determine the volumetric, 3-D bone organic matrix density. The rectangular elements in the flow diagram are herein denoted "processing blocks" and represent computer software instructions or groups of instructions.

Alternatively, the processing blocks represent steps performed by functionally equivalent circuits such as a digital signal processor circuit or an application specific integrated circuit (ASIC). It should be appreciated that some of the steps described in the flow diagram may be implemented via computer software while others may be implemented in a different manner e.g. via hardware or an empirical procedure. The flow diagrams do not depict the syntax of any particular programming language. Rather, the flow diagrams illustrate the functional information one of ordinary skill in the art requires to fabricate circuits or to generate computer software to perform the processing required of the particular apparatus. It should be noted that many routine program elements, such as initialization of loops and variables and the use of temporary variables are not shown. It will be appreciated by those of ordinary skill in the art that unless otherwise indicated herein, the particular sequence of steps described is illustrative only and can be varied without departing from the spirit of the invention.

Turning now to FIG. 3, processing begins in an image acquisition phase 38 which includes processing blocks 40 and 42. In processing block 40, a first pulse sequence fragment having a characteristic selected to suppress one or more fluid resonance signals is provided in an MRI system. In the case of imaging a bone to aid in the detection of osteoporosis, the first pulse sequence fragment suppresses at least two fluid resonance signals. Although one particular pulse sequence fragment to suppress fluid is described herein below in conjunction with FIGS. 3 and 3A, it is recognized that any technique or pulse sequence which effectively suppresses fluid signals may also be used.

Processing next proceeds to processing block 42 in which a second pulse sequence fragment having a characteristic selected such that the pulse sequence fragment images at least solids is provided to the MRI system. Since the first pulse sequence fragment substantially suppresses signals arising from fluids, when the second pulse sequence fragment is used, only signals generated in response to solids remain.

The second pulse sequence fragment can be provided, for example, as the type used in conventional solid state MRI which, as is known, detects both solid and fluid constituents. Since conventional solid state MRI techniques detect both the solid and fluid constituents, the solid constituents would normally be obscured by the fluid constituents. However, by first applying the pulse sequence fragment which suppresses fluid resonance signals, it is possible to utilize the conventional solid state MRI technique to measure the bone matrix. One example of such a pulse sequence fragment is described in U.S. Pat. No. 6,185,444.

It is also recognized that the second pulse sequence fragment may be provided as the type which detects only solid constituents. One example of such a pulse sequence fragment is described in U.S. Pat. No. 5,539,309.

The scanner loops between boxes 40 and 42. After enough data is acquired, processing proceed to step 43 in which the image is reconstructed and then results are displayed as shown in block 44.

Referring now to FIGS. 4A and 4B which when taken together are referred to as FIG. 4 below, a pulse sequence for bone matrix imaging by fat and water suppressed proton solid state projection MRI includes a first pulse sequence fragment 50 selected to suppress fluid (e.g. water and fat) signals. The first pulse sequence fragment 50 precedes a second pulse sequence fragment 52 selected to image at least solids. It should be appreciated that the first pulse sequence fragment 50 may be provided from any imaging technique which suppresses fluid signal response. Similarly, the second pulse sequence fragment 52 may be provided using any solid state imaging technique which images at least solids. The techniques described in the aforementioned U.S. Pat. Nos. 6,185,444 and 5,539,309 are appropriate for example.

In the particular example shown in FIG. 4, the first pulse sequence fragment 50 includes a first series of RF pulses 54a and a first series of gradient pulses 54b while the second pulse sequence fragment 50 includes a hard RF pulse 74 provided in the presence of a projection gradient 80 which yields a resulting Free Induction Decay (FID) signal 76.

The first series of RF pulses 54a includes a first pulse 56 corresponding to a water-selective 90° pulse 56. Pulse 56 is selected to target fluids (i.e. pulse 56 covers fluid state resonance widths) and thus is sometimes referred to as a "weak" or "soft" pulse. The water-selective 90° pulse 56 is followed by a water-selective 180° pulse 58 which in turn is followed by a fat-selective 90° pulse 60, followed by a fat-selective 180° pulse 62. It should be appreciated that reference is made herein to water and fat selective 90° and 180° pulses. It is recognized that although the target values are exactly 90° and 180°, in practice it is always the case that there is a significant (10-30 degrees or more) distribution in flip angles over the volume of the subject or specimen, and the actual central value may be far from 90° and 180° degrees.

A series of dephasing gradient pulses 64-70 is provided in conjunction with the series of water and fat selective pulses 56-62 and together the series of pulses 54a, 54b provide the first pulse sequence fragment 50 which corresponds to a fluid suppression pulse sequence fragment. Ideally, after the first pulse sequence fragment 50 has been applied, all fluid signals have been suppressed. Thus, even though the second pulse sequence fragment 52 detects both fluids and solids, since the fluid signals have been suppressed by the first pulse sequence fragment 50, only solid signals are left to detect.

It should be appreciated that fluid signals are suppressed with the sequence of frequency selective RF pulses 54a which precede the field gradient pulse 80 and RF pulse 74 of the projection imaging pulse sequence 52. Because the spectral line widths of fluids are relatively narrow compared to the line width of the matrix, and because they occur at different Larmor frequencies (separated by the chemical shift difference between water and fat), they may be excited with weak RF pulses, which excite only a narrow band of frequencies.

In principle, either water or fat could be excited with a weak 90° RF pulse, which would convert all the signal of that substance, for instance water, into transverse magnetization which would then be allowed to dephase under a field gradient pulse (the dephasing gradient). In practical systems, however, it is nearly impossible to apply a perfect 90° pulse to the entire volume of the specimen or subject. Therefore, the pulse sequence may be repeated with the addition of a 180° frequency selective pulse (e.g. pulse 58) following the first dephasing gradient 64. This inverts any residual water longitudinal magnetization to its inverse, which then contributes to the image, but in a negative sense (i.e. the 180° pulses 58, 62 compensate for residue in the 90° pulses 56, 60).

Subsequent repetitions of the pulse sequence are performed alternately with and then without the 180° pulses 58, 62 (and the accompanying dephasing gradients 66, 70), and all of the recorded signals are co-added. The residual water signals, already reduced substantially because of the 90° pulse and dephasing pulse, are alternately positive and negative in the summation but of approximately of the same magnitude, and so they largely cancel. By this method, up to about ninety-seven (97) percent of the water signal may be suppressed. The same process can then be applied to suppress the fluid fat signal.

In the combined suppression, the first pulse sequence fragment 54a contains frequency selective 90° for water and fat, accompanied by their gradient dephasing pulses, while the second repetition also includes the 180° pulses for water and fat. The pairs of pulse sequences are co-added to suppress the fluid water and fat signals. By careful choice of the frequency selective pulse amplitudes (which approximately determine the frequency bandwidth over which the pulses are effective), the effect of these pulses on the signal from the solid matrix may be minimized while retaining good fluid signal suppression.

It should be appreciated that in alternate embodiments, it may be desirable or necessary to provide a sequence in which gradient pulses 66, 70 are present for all scans (alternating the 180° pulses 58, 62 on alternate scans as before). Alternatively, either or both gradient pulses 66, 70 may be inverted in sign with respect to gradient pulses 64, 68, or may be of different amplitudes or directions with respect to gradient pulses 64, 68. Either of these approaches may result in improved fluid signal suppression.

In one embodiment, the spacing between each of the RF pulses 56-62 (e.g. the spacing between the falling edge of pulse 56 and the leading edge of pulse 58) is selected so as not to generate spin echoes in the second pulse sequence fragment 52. Alternatively, the gradient pulses 54b may be individually varied in number, sign, magnitude, direction and spacing, and the RF pulses 54a may be individually varied in number, magnitude, phase and spacing so as to maximize the suppression of fluid signals and minimize the suppression of solid signals during the image acquisition pulse sequence fragment 52. In one particular embodiment, the spacing between the falling edge of pulse 56 and the leading edge of pulse 58 is approximately 1 millisecond (ms) while the spacing between the falling edge of pulse 58 and the leading edge of pulse 60 is approximately 2 ms.

It should be noted that the transition between the last dephasing gradient pulse 70 in the first pulse sequence fragment 50 and the projection gradient 80 in the second pulse sequence fragment 52 may be accomplished via a transition pulse having a shape such as pulse 78 or transition pulse having a shape such as pulse 78'. Any shape of transition pulse 78 is within the scope of the invention. It is only necessary that gradient pulse is sufficiently stable by the time the second pulse sequence fragment 52 starts such that good image quality is achieved.

In one experiment, a pulse sequence to suppress signals contributed from both water and fat (long $T_2$) and observe signals from the solid components of bone matrix (collagen, short $T_2$) as shown in FIG. 3 was used. Low power and long duration frequency selective (resonant with water and fat sequentially) 90° pulses leave short $T_2$ magnetization (collagen) along the z-axis while rotating the long $T_2$ (water or fat) magnetization into the transverse plane; the water and fat magnetization is subsequently dephased by large gradient pulses. To further suppress the residual water and fat z-magnetization, which remains because of 90 pulse imperfections, a 180 pulse was applied following each 90 pulse on alternate scans. The 180 pulses invert only the long-$T_2$ water and fat magnetization, leaving short-$T_2$ magnetization (collagen) unaffected. A large amplitude RF pulse, of a duration short compared to the $T_2$s of the sharper collagen resonances, is applied to rotate the available z-magnetization into the transverse plane where it is acquired by a three dimensional projection imaging method. If there is any long $T_2$ signal excited by this hard pulse, it is canceled out in two consecutive scans due to the selective 180 degree pulses. Hence the only signals contributing to the image will be those arising from short $T_2$ components.

Images were taken on a 4.7 T Bruker/GE (Fremont, Calif., USA) CSI Omega MR system equipped with an Oxford Instruments (Oxford, UK) 4.7 T 33 cm horizontal bore magnet. Two different probes were used in different experiments to accommodate different size specimens. A 2.5 cm inside diameter solenoid coil was used for the water and oil phantom and trabecular bone specimens. A birdcage coil with inside diameter of 13 cm was used for larger cortical bone specimens. This coil produced a highly homogeneous $B_1$ field over the specimen volumes (at the expense of lower filling factor). The $^1$H Larmor frequency was 200.09 MHz. The water and fat selective suppression 90 degree pulses were 2.5-3.0 ms in duration, and the 180 degree pulses were 5.0-6.0 ms in duration. The 90 degree and 180 degree pulses were separated by 1 ms, the water and fat suppression pulse pairs were separated by 2 ms, and the entire suppression sequence was separated from the beginning of the gradient ramp 78' by 2 ms (these choices are chosen to interfere with water or fat echo formation during the matrix signal acquisition). The short hard pulse used to excite the solid signal was 10 microseconds in duration.

The FID projection data was acquired under fixed gradient magnitudes (60 mT/m) in 998 or 1963 directions (field of view FOV 4 or 8 cm, respectively) at a sampling rate of 5 microseconds or 25 microseconds per complex point. Effectively, about 64 complex points of the FID were used in the reconstruction. The number of gradient directions (or views) is not a "round" number, but rather is chosen to provide a uniform pattern of coverage in solid angle. The algorithm used to select projection directions distributes them on a series of parallel latitude rings equally spaced in azimuthal angle; within each ring views are spaced in equal increments of polar angle, with the number of views in each ring proportional to the sine of the azimuthal angle. This gives a pattern uniformly covering the sphere in which views are allotted to equal solid angles. Gradient pulse rise and fall times were 3 ms.

Repetition times TR were 0.5 s and the FIDs were averaged over two acquisitions with 180 degree receiver phase cycling. A typical measurement time for 998 projections (obtained in a block of 1024 acquisitions, because the Omega software requires the number of acquisitions in a block to be a power of 2) was 18 minutes, and for 1963 projections (2048 acquisitions) was 36 minutes. The fractional isotropic resolution of the reconstruction (the linear resolution element divided by the field of view) is given by sqrt (pi/N), where N is the number of projections. The spatial resolution is therefore 2.2 mm for images with FOV=4 cm (N=998) and 3.2 mm for images with FOV=8 cm (N=1963). A small additional time was required for separate collection of the weak gradient acquisitions to fill the center of k-space.

Table 1 shows the proton $T_1$ and $T_2$ measurements on individual specimens at the ambient temperature of 9° C. inside the magnet bore.

TABLE 1

|  | $T_1$(ms) | $T_2$(µs) |  |  |
|---|---|---|---|---|
| Dry EDTA Decalcified bone 1 | 419.0 | 208.5[a] |  |  |
| Dry EDTA Decalcified bone 2 | 457.0 | 176.6[a] |  |  |
| Dry Tendon 1 | 929.3 | 131.8[a] |  |  |
| Dry Tendon 2 | 1023.9 | 124.3 |  |  |
| Dry Tendon 3 | 993.0 | 119.9[a] |  |  |
|  | Water (ms) | Fat (ms) | Water (ms) | Fats (ms) |
| Bovine Intramedullary fat 1[b] | 982.4 | 262.6 | 20.4 | 18.6 |
| Bovine Intramedullary fat 2[b] | 895.0 | 251.6 | 21.8 | 16.9 |
| Bovine Intramedullary fat 3[b] | 678.0 | 294.0 | 30.0 | 15.7 |

[a]$T_2$ obtained by 1/(π × linewidth)
[b]From cancellous bone tissues

The average $T_1$s (± standard deviations) of water and lipid in bovine intramedullary fat are 850±160 ms and 270±20 ms, respectively. The average $T_2$s of water and fat are 24±5 ms and 17±1.5 ms, respectively. These results are consistent with data published in the literature. The average $T_1$ and $T_2$ of dry EDTA and HCl decalcified bone are 440±30 ms and 190±20 µs, respectively. The $T_2$ of dry tendon, 125±6 µs, is shorter than that of decalcified bone, while the $T_1$ is longer at 980±50 ms. These results provide the basis for the choice of the water and fat suppression pulse lengths.

Figures 5A, 5B:
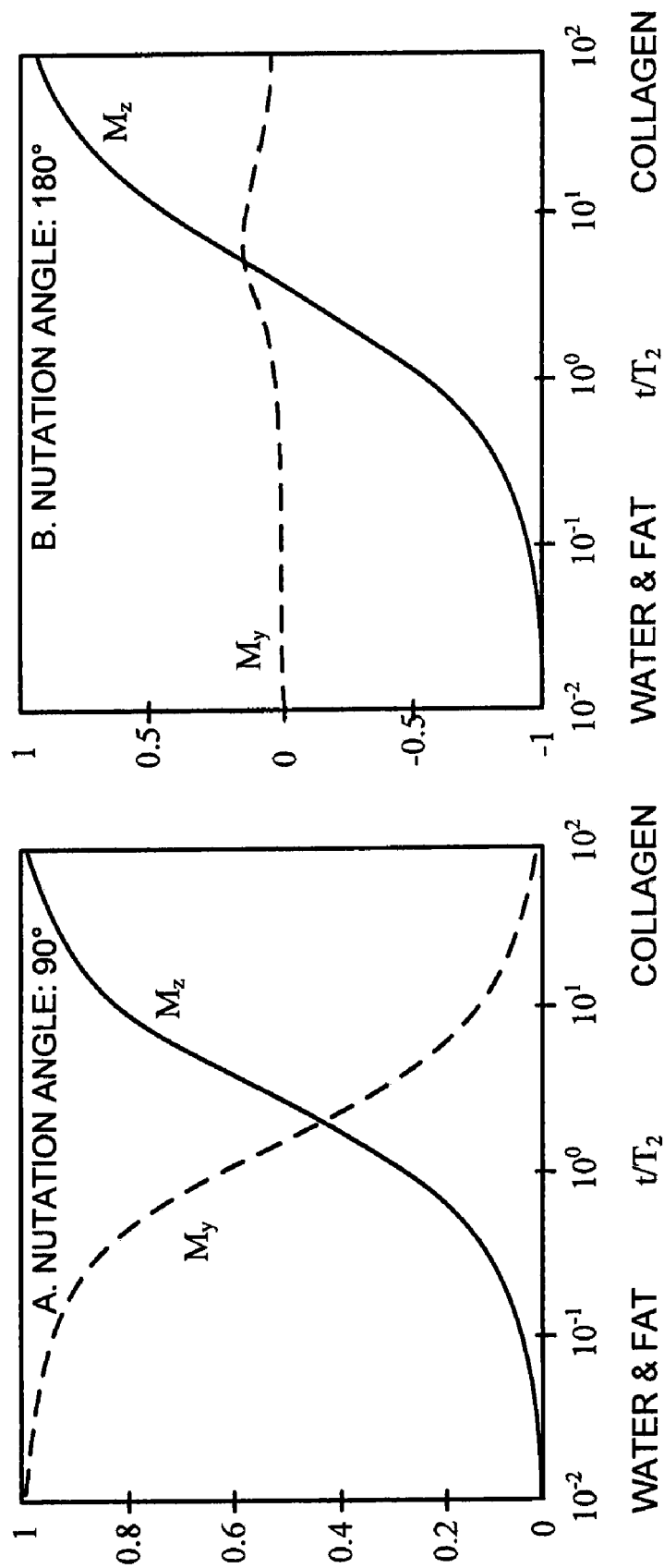
FIGS. 5A and 5B are plots of transverse and longitudinal components respectively of magnetization M following rectangular RF pulses.

FIGS. 5A and 5B are plots of transverse $M_y$ and longitudinal $M_z$ components of magnetization M (originally along z) versus $t/T_2$ following perfect rectangular RF pulses. FIG. 5A illustrates the $\gamma B_1 t = \pi/2$ pulse: the magnetization of small $t/T_2$ (water and fat) constituents is rotated into the transverse plane, while the magnetization of large $t/T_2$ constituents (solid collagen and motionally restricted matrix water) is preserved along the z-direction. FIG. 5B illustrates the $\gamma B_1 t = \pi$ pulse: The initial magnetization of small $t/T_2$ constituents is inverted, while the magnetization of large $t/T_2$ constituents is preserved along the z-direction. Little transverse magnetization is created irrespective of the value of $t/T_2$.

According to FIGS. 5A and 5B, in the long $T_2$ regime, if $t/T_2 \sim 0.1$, more than 95% of M would be flipped into the transverse plane by the soft 90° pulse. In the short $T_2$ regime, if $t/T_2 \sim 10$, only 80% of M would be unaffected by the soft 90° pulse, but if $t/T_2 \sim 20$, the percentage of M unaffected would increase to 90%. A pulse length of 2.5-3.0 ms was therefore selected for the soft 90° pulse (suppression pulse). The choice of the 180° pulse length is more heavily influenced by the desire to not affect the short $T_2$ component when inverting the long $T_2$ component. The 180° soft pulse was chosen to be applied at the same power level but twice the duration of the soft 90° pulse. When applied in vivo at 37° C., the increased molecular mobility of water and fat will make the selective pulses work somewhat more effectively than in the present experiments.

Figure 6:
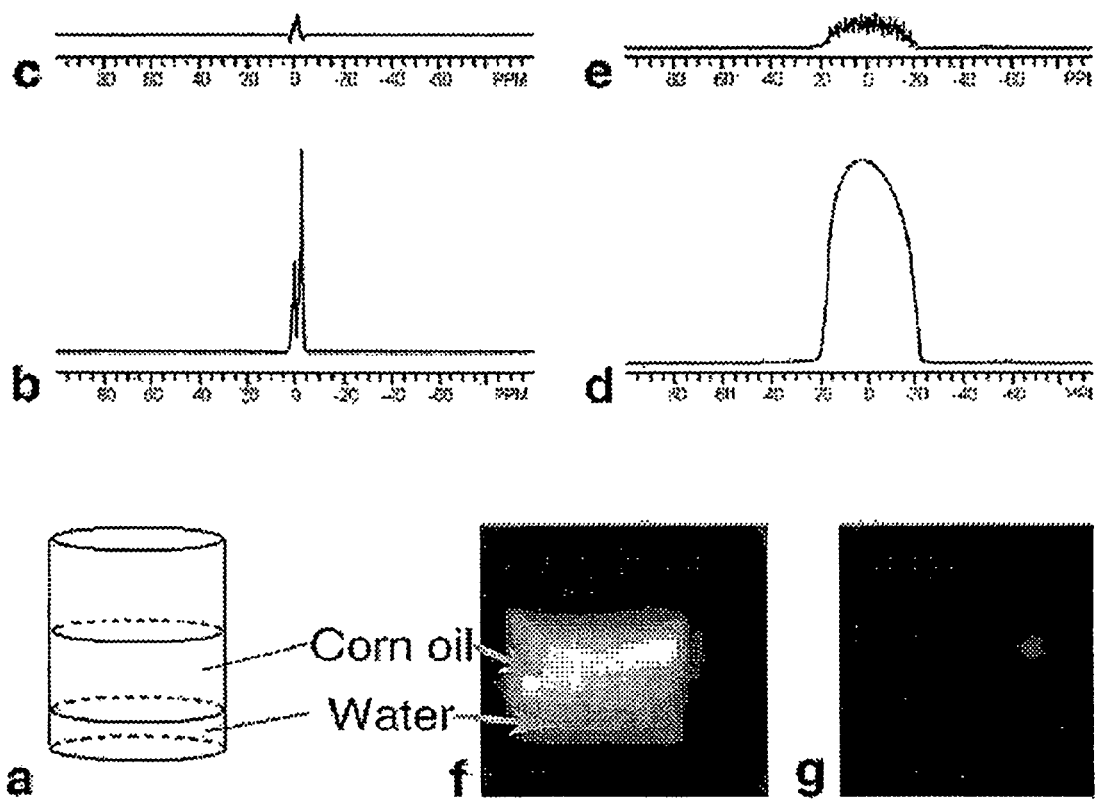
FIG. 6A is a schematic illustration of a phantom of corn oil and water.
FIG. 6B is a schematic illustration of a single pulse proton spectrum of the phantom.
FIG. 6C is a schematic illustration of a spectrum of the phantom following application of the water and fat suppression sequence.
FIG. 6D is a schematic illustration of a one dimensional total proton projection image profile of the phantom without water and fat suppression.
FIG. 6E is a schematic illustration of a water and fat suppressed projection imaging profile of the phantom.
FIG. 6F is a single plane from a 3D total proton projection image of the phantom.
FIG. 6G is a single plane from a 3D water and fat suppressed projection image of the phantom.

FIG. 6A demonstrates the water and fat suppression performance on a phantom (a 2.5 cm diameter vial containing a layer of corn oil and a layer of water, FIG. 6A). These experiments used the 2.5 cm solenoid coil. The regular (no suppression) one pulse proton spectrum of the phantom shows the water and fat peaks 3.5 ppm apart (FIG. 6B). The spectrum, acquired by water and fat suppressed projection imaging without the projection gradients, showed that these two peaks were mostly suppressed (FIG. 6C). One-dimensional proton MRI of the phantom by standard FID projection imaging (FIG. 6D) and water and fat suppressed projection imaging (FIG. 6E) shows that the profile of the phantom is mostly suppressed by water and fat suppressed projection imaging. The percentage of suppression was calculated by comparing standard three-dimensional FID projection (FIG. 6F) and water and fat suppressed projection imaging (FIG. 6G) image intensities over the major portion of the images (excluding the bright spots in the boundary area where RF inhomogeneity near the coil wires causes the method to fail). This calculation shows that more than 97% of signal from both water and fat was suppressed.

Figure 7:
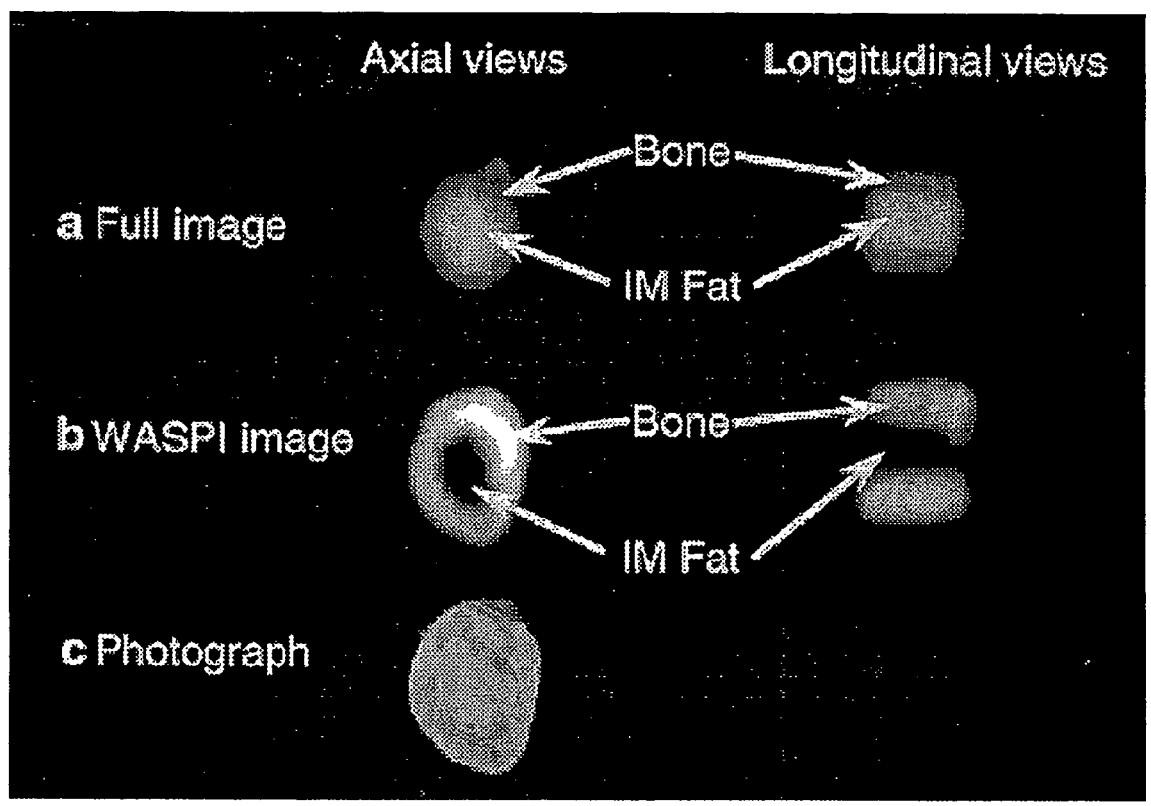
FIG. 7A is a pair of single planes from a 3D total proton projection image of a bovine femur diaphysis with intramedullary (IM) fat intact in the intramedullary cavity.
FIG. 7B is a pair of single planes from a water and fat suppressed projection image of a bovine femur diaphysis with intramedullary (IM) fat intact in the intramedullary cavity showing that the signal from all material in the intramedullary cavity is suppressed.
FIG. 7C is a photograph of the a bovine femur diaphysis with intramedullary (IM) fat.

Standard proton three-dimensional FID projection imaging (yielding the total proton signal) and WASPI (yielding the matrix signal) were performed on an intact diaphyseal cortical bone specimen containing its solid intramedullary fat mass (which contains water as well as lipid), using the 13 cm diameter birdcage coil with FOV~8 cm. Because of its greater molecular mobility compared to collagen, the intramedullary fat signal is much brighter than that of cortical bone in the regular projection image (FIG. 7A). In the water and fat suppressed projection images, the intramedullary fat is no longer visible (FIG. 7B). Quantitatively, the intramedullary fat signal is found to be less than 3% of its normal value, while the cortical bone signal is reduced to 40% of its normal value. A significant loss of cortical bone signal is expected because some solid matrix signal loss results from the suppression pulses, and because cortical bone contains water and a small amount of lipid which are fully suppressed. This experiment convincingly demonstrates that what is observed in water and fat suppressed projection imaging is basically the solid, lipid free, dry organic matrix of compact cortical diaphyseal bone.

Figure 8:
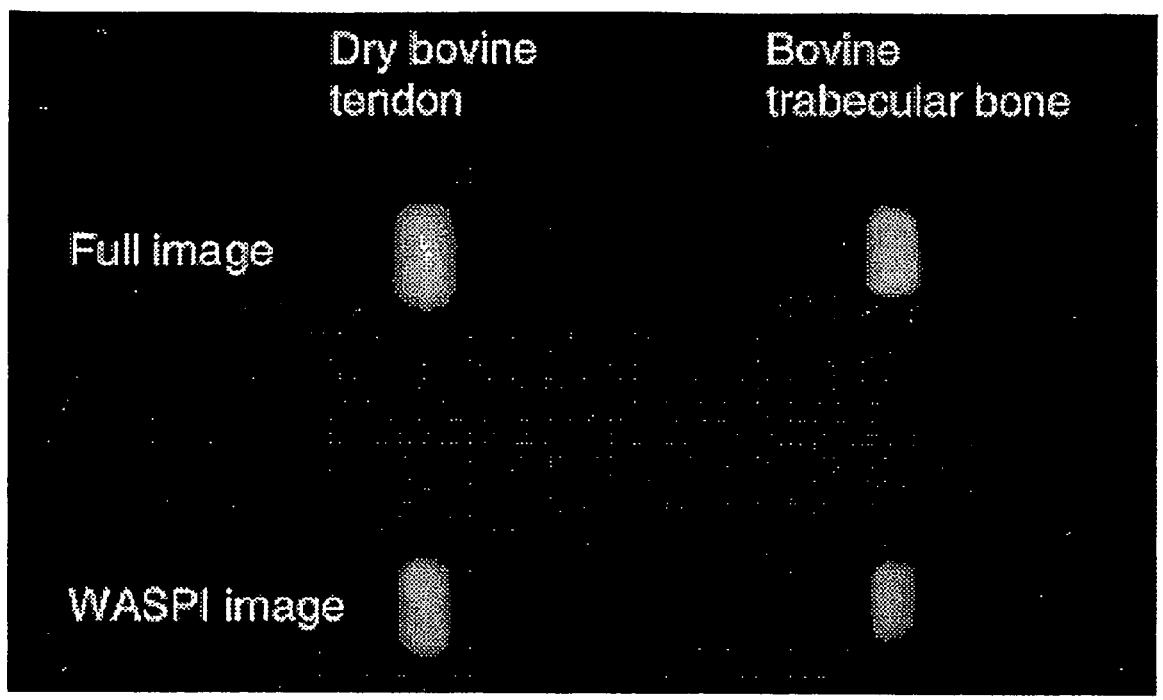
FIG. 8 is a series of single planes from the proton total and 3D water and fat suppressed projection images of dry tendon and trabecular bone.

Regular and water and fat suppressed projection images with FOV~4 cm (FIG. 8) were obtained from cancellous, trabecular bone specimens. The intensity of the bone signal in the water and fat suppressed projection images is assumed to arise from the solid, lipid free, dry organic matrix constituents of the bone substance of the trabeculae in the cancellous bone tissue. In order to compare MRI data with chemical analysis, the outcome of which is an average over the whole specimen, the MRI signal was averaged over all pixels whose signal is at least 10 times higher than the average background pixel. The intensity of dry bovine tendon was also measured in the same manner using the same experimental procedures as a standard for water and fat suppressed projection imaging. In water and fat suppressed projection imaging of dry tendon, the signal is reduced to 70% of its normal value. The intensity ratio of the water and fat suppressed projection image of the very young trabecular bone divided by the tendon water and fat suppressed projection image gives the approximate weight percentage of the lipid free, dry bone matrix. The weight percentages, calculated from the image intensity ratio, for two specimens are 21% and 18% respectively. Gravimetric analyses of identical specimens taken from the same bones yielded weight percentages of dry organic matrix in wet bone tissue of 17% and 16% respectively. This reasonable agreement in determinations of organic matrix content by the two different methods confirms the general validity of the water and fat suppressed projection imaging technique. It should be appreciated in FIG. 6 that the display brightness of the water and fat suppressed projection images has been increased to show the specimens clearly. However, for purposes of calculating the matrix density (directly measured as volumetric 3-D data), the actual pixel values are used.

All references cited herein are hereby incorporated herein by reference in their entirety.

Having described preferred embodiments of the invention, it will now become apparent to one of ordinary skill in the art that other embodiments incorporating their concepts may be used.

For example, although the use of this technique for measuring the volumetric, 3-D bone organic matrix is likely to be important, other applications are possible, and are within the scope of the invention. These other applications include any situation in which at least two substances are present which differ in their spin-spin relaxation time, and it is desired to produce an MR image of the shorter spin-spin relaxation time material without interference from the longer spin-spin relaxation time material. Examples include without limitation biological and nonbiological composite materials such as tendon, cartilage, ligament, plaques, fibrotic tissue, calcified tissue, skin, hair, nail, hoof, cuticle, leather, parchment and other hard or soft or fluid animal tissues and their derivatives, wood and other plant tissues and their derivatives, fibers, foods, agricultural materials, soil, coal, petroleum, tar, oil shale, minerals, rock, fossils, animal and plant remains and other geophysical or petrochemical materials, liquids, gases, chemicals, polymers, rubbers, ceramics, composite materials, sols, gels, colloids, porous materials and liquid crystalline materials, either singly or in combination. Nuclear isotopes other than protons, including without limitation $^2H$, $^{13}C$, $^{14}N$, $^{15}N$, $^{17}O$, $^{19}F$, $^{23}Na$ and $^{31}P$, and other substances with magnetic moments, including without limitation electrons, neutrons, muons, ferromagnetic, antiferromagnetic and ferrimagnetic materials, are also within the scope of the invention.

It should be appreciated that Variations of the fluid (e.g. water and fat) suppression pulse parameters, including numbers, substances to be suppressed, numbers of pulses, pulse durations, interpulse durations, pulse flip angles, pulse RF phases, pulse amplitudes and pulse shapes, whether used in combination with projection imaging or other imaging pulse sequences, irrespective of the number of spatial dimensions, are all within the scope of the invention.

It is felt therefore that these embodiments should not be limited to disclosed embodiments, but rather should be limited only by the spirit and scope of the appended claims.

What is claimed is:

1. A method for producing an image using a magnetic resonance imaging (MRI) system, the steps comprising:
    a) performing a first preparatory stage of an MR pulse sequence to suppress a transverse magnetization of a first spin-species having a first $T_2$ relaxation time;
    b) performing a first imaging stage of the MR pulse sequence using projection imaging to sample a first free induction decay signal from a second spin species having a $T_2$ relaxation time substantially shorter than the first $T_2$ relaxation time and produce a first image data set;
    c) performing a second preparatory stage of the MR pulse sequence to suppress the transverse magnetization of the first spin-species and invert a longitudinal magnetization of a desired spin-species;
    d) performing a second imaging stage of the MR pulse sequence using projection imaging to sample a second free induction decay signal from the second spin species and produce a second image data set; and
    e) reconstructing the first and second image data sets to produce an MR image including the second spin species that is substantially free of the first spin-species.

2. The method as recited in claim 1 wherein the first spin species include at least one of fat and water and the second spin species includes components from bone.

3. The method as recited in claim 1 wherein the first preparatory stage of the MR pulse sequence includes selective 90 degree RF pulses and the second preparatory stage of the MR pulse sequence includes selective 90 degree RF pulses and 180 degree RF pulses.

4. The method as recited in claim 3 wherein the selective 90 degree RF pulses are approximately 2.5 ms to 3.0 ms in duration.

5. The method as recited in claim 4 wherein the 180 degree RF pulses are approximately 5.0 ms to 6.0 ms in duration.

6. The method as recited in claim 3 wherein the first and second imaging stages include nonselective 90 degree RF pulses.

7. The method as recited in claim 6 wherein the nonselective 90 RF pulses are approximately 10 µs in duration.

8. The method as recited in claim 1 wherein the MR image includes information relating to a degree of bone mineralization.

9. The method as recited in claim 8 further including f) comparing the MR image produced in step e) to a bone mineral density measurement produced using solid state $^{31}P$ projection MRI to determine the degree of bone mineralization.

10. The method as recited in claim 1 wherein steps a) to d) are repeated at a given repetition time to acquire a desired amount of NMR data before the reconstruction of the MR image at step e).

11. The method as recited in claim 10 wherein the given repetition time is approximately 0.5 s.

12. A method for producing an image using a magnetic resonance imaging (MRI) system, the steps comprising:
    a) performing a first preparatory stage of an MR pulse sequence to suppress a magnetization of a first spin-species having a first $T_2$ relaxation time;
    b) performing a first imaging stage of the MR pulse sequence to sample a first free induction decay signal from a second spin species having a $T_2$ relaxation time substantially shorter than the first $T_2$ relaxation time and produce a first image data set;

c) performing a second preparatory stage of the MR pulse sequence to suppress a magnetization of the first spin-species and invert a magnetization of a desired spin-species;

d) performing a second imaging stage of the MR pulse sequence to sample a second free induction decay signal from the second spin species and produce a second image data set; and e) reconstructing the first and second image data sets to produce an MR image including the second spin species that is substantially free of the first spin-species to illustrate a degree of bone mineralization.

13. The method as recited in claim 12 wherein the first spin species include at least one of fat and water and the second spin species includes bone.

14. The method as recited in claim 12 wherein the first preparatory stage of the MR pulse sequence includes selective 90 degree RF pulses and the second preparatory stage of the MR pulse sequence includes selective 90 degree RF pulses and 180 degree RF pulses.

15. The method as recited in claim 14 wherein the first and second imaging stages include nonselective 90 degree RF pulses.

16. The method as recited in claim 2 further including f) comparing the MR image produced in step e) to a bone mineral density measurement produced using solid state $^{31}$P projection MRI to quantify the degree of bone mineralization.

17. The method as recited in claim 12 wherein step a) includes performing the first preparatory stage of an MR pulse sequence to suppress a transverse magnetization of the first spin-species having a first $T_2$ relaxation time, and step c) includes performing the second preparatory stage of the MR pulse sequence to suppress a transverse magnetization of the first spin-species and invert a longitudinal magnetization of the desired spin-species.

* * * * *

UNITED STATES PATENT AND TRADEMARK OFFICE
CERTIFICATE OF CORRECTION

PATENT NO.      : 7,574,248 B2  
APPLICATION NO. : 10/514616  
DATED           : August 11, 2009  
INVENTOR(S)     : Ackerman et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1241 days.

Signed and Sealed this

Seventh Day of September, 2010

David J. Kappos  
*Director of the United States Patent and Trademark Office*

UNITED STATES PATENT AND TRADEMARK OFFICE
CERTIFICATE OF CORRECTION

| | | |
|---|---|---|
| PATENT NO. | : 7,574,248 B2 | Page 1 of 1 |
| APPLICATION NO. | : 10/514616 | |
| DATED | : August 11, 2009 | |
| INVENTOR(S) | : Jerome L. Ackerman et al. | |

It is certified that error appears in the above-identified patent and that said Letters Patent is hereby corrected as shown below:

In the Specification

Please insert the following after the first paragraph in Column 1, Line 4:
--STATEMENT REGARDING FEDERALLY SPONSORED RESEARCH
This invention was made with government support under AR042258, and AR014701 awarded by the National Institutes of Health. The government has certain rights in the invention.--.

Signed and Sealed this
Ninth Day of May, 2023

Katherine Kelly Vidal
*Director of the United States Patent and Trademark Office*